(12) United States Patent
Nicolau et al.

(10) Patent No.: US 7,060,270 B2
(45) Date of Patent: Jun. 13, 2006

(54) METHODS AND COMPOSITIONS OF MONOCLONAL ANTIBODIES SPECIFIC FOR BETA-AMYLOID PROTEINS

(75) Inventors: Yves Claude Nicolau, Newton, MA (US); Ruth Greferath, Kehl (DE)

(73) Assignee: Diagenics International Corporation, Woburn, MA (US)

( * ) Notice: Subject to any disclaimer, the term of this patent is extended or adjusted under 35 U.S.C. 154(b) by 390 days.

(21) Appl. No.: 10/288,557

(22) Filed: Nov. 4, 2002

(65) Prior Publication Data

US 2003/0108551 A1 Jun. 12, 2003

Related U.S. Application Data

(60) Provisional application No. 60/336,514, filed on Nov. 2, 2001.

(51) Int. Cl.
*A61K 39/395* (2006.01)
*C12P 21/08* (2006.01)

(52) U.S. Cl. ................................. 424/141.1; 530/388.1
(58) Field of Classification Search ............ 530/387.1, 530/388.1; 424/130.1
See application file for complete search history.

(56) References Cited

U.S. PATENT DOCUMENTS

| | | | |
|---|---|---|---|
| 6,214,565 B1 | 4/2001 | Prusiner et al. | |
| 6,710,226 B1 * | 3/2004 | Schenk | 800/12 |
| 2002/0086847 A1 | 7/2002 | Chain | |
| 2002/0136718 A1 | 9/2002 | Raso | |
| 2002/0156036 A1 * | 10/2002 | Nicolau | |
| 2003/0232758 A1 * | 12/2003 | St. George-Hyslop et al. | |

OTHER PUBLICATIONS

Solomon et al. 1996. PNAS 93:452-455.*
Sigma catalog, 2000. pp. 1 and 1196.*
Seubert et al. 1992. Nature 359:325-327.*
Legleiter et al. 2004. J Mol Biol 335:997-1006.*
Dodart et al. 2002. Nature Neuroscience 5:452-457.*
Eckert et al. 2003. Annals of the New York Academy of Sciences 1010:604-609.*
Luo et al. 2002. PNAS 99:12202.*
Rohn et al. 2001. Neurobiology of Disease 8:1006-1016.*
Kotillnek et al. 2002. J Neurosci 22:6331-6335.*
Harlow et al. 1988. Antibodies: A Laboratory Manual. pp. 71-82.*
Robinson 1992. Immunology 76:593-598.*
Rohn et al., "A Monoclonal Antibody to Amyloid Precursor Protein Induces Neuronal Apoptosis", Journal of Neurochemistry, Jun. 2000, vol. 74, No. 6, pp. 2331-2342.
Matsunaga et al., "A pH-dependent conformational transition of Abeta peptide and physiochemical properties of the conformers in the glial cell", Biochem. J., Feb. 2002, vol. 361, pp. 547-556.
Sudo et al., "Antibody-Regulated Neurotoxic Fuction of Cell-Surface beta-Amyloid Precursor Protein", Molecular and Cellular Neuroscience, Dec. 2000, vol. 16, No. 6, pp. 708-723.

* cited by examiner

*Primary Examiner*—Sharon Turner
*Assistant Examiner*—Daniel E. Kolker
(74) *Attorney, Agent, or Firm*—Alleman Hall McCoy Russell & Tuttle LLP

(57) ABSTRACT

This invention provides methods and compositions for the detection, diagnosis and treatment of amyloid-associated diseases, in particular, diseases comprising deposition of amyloid assemblies, fibrils, filaments, tangles, or plaques. A preferred composition comprises monoclonal antibodies that specifically bind amyloid proteins, peptides or fragments and change the conformation.

5 Claims, 9 Drawing Sheets

METHODS AND COMPOSITIONS OF MONOCLONAL ANTIBODIES SPECIFIC FOR BETA-AMYLOID PROTEINS

RELATED APPLICATIONS

This application claims benefit of U.S. Provisional Application No. 60/336,514 filed Nov. 2, 2001, which is herein incorporated in its entirety.

FIELD OF THE INVENTION

The present invention relates to compositions and methods for the diagnosis and treatment of diseases, particularly amyloid-associated diseases. In particular, the invention comprises monoclonal antibodies to beta-amyloid protein that are capable of changing the conformation of the amyloid protein.

BACKGROUND OF THE INVENTION

Amyloid protein deposition is associated with cognitive decline in millions of Americans. Amyloid proteins can be deposited in extracellular neufibrillary tangles, within classical or diffuse senile plaques, and in vessel walls. Amyloid plaques in the brain are predominantly composed of (beta) β-amyloid, a 4 kD of protein, 39–43 residues. Beta-amyloid is expressed by a gene located on chromosome 21 and is derived by proteolytic cleavage of a much larger (770 residue) cell protein called amyloid precursor protein (APP). After excision, β-amyloid is polymerized into amyloid filaments, which in turn aggregate into visible amyloid plaque deposits. Amyloid-associated diseases include, but are not limited to, Alzheimer's disease, Lewy body dementia, Down's syndrome, hereditary cerebral hemorrhage with amyloidosis (Dutch type), and the Guam Parkinson-Dementia complex. Beta-amyloid plaques also occur in persons who have sustained a head trauma, critical coronary disease, and other disease processes. While β-amyloid is found predominantly in the nervous system, it is also present in non-neural tissue.

One example of amyloid-associated diseases is Alzheimer's disease. Alzheimer's disease (AD) is the most common disease caused by amyloid plaque deposition. It is characterized by neuronal loss, neurofibrillary tangles, and neuritic plaques comprised of β-amyloid. This neurodegenerative illness proceeds in stages, gradually destroying memory, reason, judgment, language, and eventually the ability to carry out even the simplest of tasks. Alzheimer's Disease affects approximately four million Americans and has been estimated to cost the nation $80 to $90 billion a year. It strikes 17 to 20 million people worldwide. Persons as young as 40–50 years of age can develop AD. Yet, because the presence of the disease is difficult to diagnose without dangerous brain biopsy, the time of onset is unknown. The prevalence of AD increases with age, with estimates of the affected population reaching as high as 40–50% by ages 85–90.

Evidence that abnormalities in β-amyloid metabolism are involved in the development of AD is found in the discovery of point mutations in the amyloid precursor protein in several rare families with an autosomal dominant form of AD. These mutations occur near the N- and C-terminal cleavage points necessary for the generation of β-amyloid from its precursor protein. Genetic analysis of a large number of AD families has demonstrated, however, that AD is genetically heterogeneous. Linkage to chromosome 21 markers is shown in only some families with early-onset AD and in no families with late-onset AD. Recently, a gene was identified on chromosome 14 whose product is predicted to contain multiple transmembrane domains and resembles an integral membrane protein. This gene may account for up to 70% of early-onset autosomal dominant AD. Preliminary data suggests that this chromosome 14 mutation causes an increase in the production of β-amyloid. A mutation in a very similar gene has been identified on chromosome 1 in Volga German kindreds with early-onset AD.

AD is definitively diagnosed through the examination of brain tissue, usually at autopsy. The currently recommended "minimum microscopic criteria" for AD diagnosis is based on the number of neuritic plaques found in brain. The amyloid cores of these neuritic plaques are composed of β-amyloid arranged in a predominately beta-pleated sheet configuration. Brain amyloid is readily demonstrated by staining brain sections with thioflavin S or Congo red. Congo red-stained amyloid is characterized by a dichroic appearance, exhibiting a yellow-green polarization color. The dichroic binding is the result of the beta-pleated sheet stricture of the amyloid proteins.

It is very difficult to diagnose Alzheimer's disease before death, to develop drug therapies, or to treat AD. Screening for the apolipoprotein E genotype has been suggested as an aid in the diagnosis of AD. Immunoassay methods have been developed for detecting the presence of neurochemical markers in AD patients and to detect an AD-related amyloid protein in cerebral spinal fluid. But these methods for diagnosing AD have not been proven to detect AD in all patients, particularly at early stages of the disease. They are also relatively invasive, requiring a spinal tap. Radiolabeled A [beta] peptide has been used to label diffuse, compact and neuritic type plaques in sections of AD brain. These peptides, however, do not normally cross the blood-brain barrier in amounts necessary for imaging in vivo.

Congo red may be used for diagnosing amyloidosis in vivo in non-brain parenchymal tissues. But Congo red is probably not suitable for in vivo diagnosis of β-amyloid deposits in the brain because only 0.03% of an injected dose of iodinated Congo red can enter the brain parenchyma. Radioiodinated bisdiazobenzidine compounds related to Congo red, such as Benzo Orange R and Direct Blue 4, have been proposed to be useful in vitro and in vivo to detect the presence and location of amyloid deposits in an organ of a patient. Many compounds contain strongly acidic sulfonic acid groups which severely limit entry of these compounds into the brain.

The inability to assess amyloid deposition in AD until after death impedes the study of this devastating illness and researchers' ability to develop effective therapies targeted at preventing or reversing β-amyloid deposition. It remains of utmost importance, therefore, to develop a safe and specific method for diagnosing AD prior to death by imaging amyloid in brain parenchyma in vivo. Moreover, recent studies have shown that damage to CNS neurons due to Alzheimer's disease begins years before clinical symptoms are evident, suggesting that therapy could begin in the pre-symptomatic phase of the disease if a sensitive diagnostic test and targeted therapies were available.

What is therefore needed are compositions and methods for detecting, diagnosing and treating diseases associated with amyloid protein, amyloid-associated diseases.

SUMMARY OF THE INVENTION

In accordance with the present invention, compositions and methods are provided that are effective in detecting, diagnosing and treating amyloid-associated conditions and diseases, particularly amyloid-associated neurodegenerative diseases. This invention is particularly useful in the detection, diagnosis and treatment of amyloid-associated diseases, including but not limited to, head trauma, critical coronary disease, nonneural amyloid-associated conditions, Alzheimer's disease, Lewy body dementia, Down's syndrome, hereditary cerebral hemorrhage with amyloidosis (Dutch type), and the Guam Parkinson-Dementia complex.

The compositions of the invention comprise monoclonal antibodies that are specific for epitopes on the beta-amyloid protein. A preferred monoclonal antibody is R7CN, which was deposited with the DSMZ (DSMZ-Deutsche Sammlung von Mikrooganismen und Zellkulturen GmbH, Mascheroder Weg 1b D-38124 Braunschweig. Germany) on Jan. 8, 2003 and assigned Accession No. DSM ACC2581. Compositions comprising such monoclonal antibodies are used in methods for detection, diagnosis and treatment of amyloid-associated diseases.

The present invention additionally comprises methods of making monclonal antibodies having the same reactivities and specificities as the monoclonal antibodies disclosed herein or altering the monoclonal antibodies disclosed herein, such as by humanizing the monoclonal antibodies. For example, making monoclonal antibodies that have the same specificity as the the monoclonal antibody R7CN or altering the monoclonal antibody R7CN using methods such as humanization, phage display technology, transgenic animals, gene shuffling, and gene sequence arrangement methods.

The present invention further comprises hybridoma cell lines, particularly those cell lines capable of producing the monoclonal antibodies of Chart1, most particularly the hybridoma cell line capable of producing the monoclonal antibody R7CN.

Compositions comprising the monoclonal antibodies, antibody derivatives or fragments thereof, specific for epitopes on the beta-amyloid protein may be administered alone or in combination with other therapeutic agents. Such adminstration may be simultaneously or sequentially.

The compositions of the present invention are used in methods for detecting amyloid proteins such as in immunoassays including radioimmunoassays, ELISAs and sandwich immunoassays. The present invention additionally comprises methods of diagnosing amyloid-associated diseases comprising contacting a labeled monoclonal antibody, such as R7CN, with a body fluid or tissue sample and measuring the amount of immunospecific binding. The present invention also relates to a diagnostic kit for use in detecting the presence of amyloid protein in a biological sample.

The compositions of the present invention are usefull in methods for treating amyloid-associated diseases. The compositions comprising monoclonal antibodies specific for amyloid protein are administered to persons with amyloid-associated disease. The compositions are effective in solubilizing the amyloid protein fibers, altering the neurotoxicity of the fibers, stopping the apoptotic cascade in effected cells, and effecting the activity of caspases. In amyloid-associated diseases in which memory loss is a symptom, the compositions of the present invention are useful in restoring or aiding in memory function.

This and other objects, features, and advantages of the present invention will become apparent after a review of the following detailed description of the disclosed embodiments and the appended claims.

DETAILED DESCRIPTION

Figure 1:
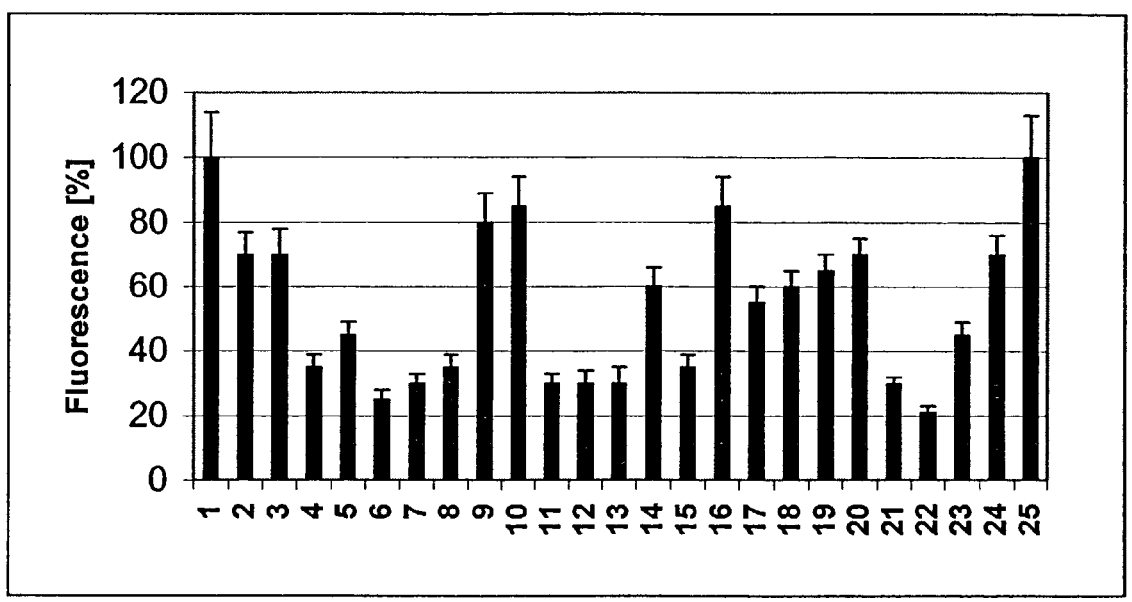
FIG. 1 is a chart showing the disaggregation of $A\beta_{1-42}$ fibers on day 8, two days after supernatants of hybridoma subclones were added.

The present invention is directed to composition and methods for detecting, diagnosing and treating amyloid-associated diseases. In particular, preferred compositions comprise antibodies, preferably monoclonal antibodies, that bind to epitopes of amyloid protein. Amyloid-associated diseases include diseases or pathologies in which beta-amyloid, or its fragments or precursors are implicated as a causative or resultant agent in the particular pathology or disease, and such pathologies or diseases include but are not limited to, head trauma, critical coronary disease, nonneural amyloid protein abnormalities, Alzheimer's disease, Lewy body dementia, Down's syndrome, hereditary cerebral hemorrhage with amyloidosis (Dutch type), and the Guam Parkinson-Dementia complex. Preferred embodiments of the compositions of the present invention comprise the monoclonal antibodies of Chart 1, and preferably the monoclonal antibody R7CN, deposited with the DSMZ (DSMZ-Deutsche Sammlung von Mikrooganismen und Zellkulturen GmbH, Mascheroder Weg 1b D-38124 Braunschweig, Germany) on Jan. 8, 2003 and assigned Accession No. DSM ACC2581.

As used herein, amyloid protein, $\beta$-amyloid, or $\delta$-amyloid protein ($A\beta$), refers to the small, approximately 4 kD protein, that is a cleavage protein of APP, amyloid precursor protein. In general, it is thought that $A\beta$ is a 39–43 residue protein, produced by sequential proteolytic processing of APP, and secreted from the cells. $A\beta_{1-42}$ refers to the form of $A\beta$ with 42 amino acid residues. It is currently believed that β-amyloid can be found in at least four forms in the body, as components of plaques, extracellular fibers, a soluble α-helix conformation in the blood and as deposits on vessel walls. Aβ filaments, or possibly intermediate protofilaments, are toxic to neurons and are thought to lead to the neurodegeneration that underlies the decline of cognitive functions.

In general, as used herein, the terms polypeptide, peptide, protein, and protein fragments are used interchangeably and can encompass modifications of such proteins. It will be appreciated that many amino acids, including the terminal amino acids, may be modified in a given polypeptide, either by natural processes, such as processing and other post-translational modifications, or by chemical modification techniques. Modifications which may be present in polypeptides or may be made to polypeptides of the invention include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, and transfer-RNA mediated addition of amino acids to proteins such as arginylation, and ubiquitination.

Antibodies as used herein include, but are not limited to, polyclonal, monoclonal, multispecific, human, humanized, chimeric antibodies, single chain antibodies, Fab fragments, F(ab') fragments, fragments produced by a Fab expression library, and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (i.e., IgG, IgE, IgM, IgD, IgA and IgY), class (i.e., IgG1, IgG2, IgG3, IgG4, IgA1 and IgA2) or subclasses of immunoglobulin molecule.

The term antibody also encompasses fragments of antibodies that include, but are not limited to, Fab, Fab' and F(ab')2, Fd, single-chain Fvs (scFv), single-chain antibodies, disulfide-linked Fvs (sdFv) and fragments containing either a VL or VH domain. Antigen-binding antibody fragments, including single-chain antibodies, may contain the variable region(s) alone or in combination with the entirety or a portion of the hinge region. Also included are antigen-binding fragments also containing any combination of variable region(s) with a hinge region. Antibodies may be from any animal origin including birds and mammals, including human, murine (i.e., mouse and rat), donkey, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin, which libraries do not express endogenous immunoglobulins, as described, for example in, U.S. Pat. No. 5,939,598, herein incorporated by rereference in its entirety.

The antibodies described herein may have differing specificities for example, monospecific, bispecific, trispecific or of greater multispecificity. Multispecific antibodies may be specific for different epitopes of a polypeptide molecule or may be specific for both a polypeptide epitope as well as for a heterologous epitope. Antibodies may also be described or specified in terms of their cross-reactivity. In one embodiment, antibody receptors include antibodies that bind analogs, orthologs, or homologs of a polypeptide. Antibodies that bind polypeptides with at least 95%, 90%, 85%, 80%, 75%, 70%, 65%, 60%, 55%, and 50% identity (as calculated using methods known in the art) to a target polypeptide are also included.

Fusion proteins, as used herein, include antibodies that are recombinantly fused to a heterologous polypeptide at the N- or C-terminus or chemically conjugated (including covalently and non-covalently conjugations) to polypeptides or other compositions. For example, antibodies may be recombinantly fused or conjugated to molecules useful as labels in detection assays, effector molecules or transport molecules, such as, for example, heterologous polypeptides, drugs, radionuclides, transferrin, proteins that cross the blood/brain barrier or toxins. See, i.e., PCT publications WO 92/08495; and WO 91/14438, among others, each of which is incorporated herein in its entirety.

Antibodies include antibody derivatives that are modified, by for example, glycosylation, acetylation, pegylation, phosphorylation, amidation, derivatization by known protecting/blocking groups, proteolytic cleavage, linkage to a cellular ligand or other protein, or other known techniques.

Attempts have been made by others to develop monoclonal antibodies as probes for imaging amyloid plaques. For instance, antibodies raised against the N-terminal region (1-28) of β-amyloid protein bind to in vitro formed β-amyloid assemblies, leading to disaggregation of fibrils and partial restoration of β-amyloid solubility. Some of the monoclonal antibodies raised against soluble β-amyloid (1-28) have also been found to inhibit fibrillar aggregation of β-amyloid peptide in vitro.

It was theorized by Bard et al., Nat. Med. 6, 916–919 (2000), that the effect of antibodies was to opsonize amyloid plaques, which were subsequently destroyed by the macrophages of the microglia. DeMattos et al., PNAS USA 98, 8850–5855 (2001), indicated that a mAB directed against the central domain of β-amyloid protein was able to bind and completely sequester plasma amyloid protein. One theory of the mechanism of action of the monoclonal used was that the presence of this mAb in circulation shifted the equilibrium of β-amyloid protein between brain and plasma, favoring peripheral clearing and catabolism instead of deposition within the brain.

In a particular embodiment of the present invention, a monoclonal antibody of the present invention, R7CN, directly interacts with amyloid protein and causes solubilization of the amyloid protein fibers. Though not wishing to be bound by any particular theory, it is theorized that direct interaction of a monoclonal antibody, raised against palmitoylated amyloid protin, such as $A\beta_{1-16}$, in liposomes, induces extensive solubilization of amyloid fibers, and the amyloid proteins lose their cytotoxic activity via an antibody-induced conformational transition in the proteins. Thus, the present invention comprises antibodies and compositions comprising those antibodies that are capable of causing a conformation transition in amyloid proteins. Preferably, these antibodies are monoclonal antibodies. The antibodies that have the functional characteristic of causing a conformational transition in amyloid protein include those antibodies that bind or are reactive with amyloid peptides comprising a range of about $A\beta_1$ to $A\beta_{1-42}$, and all peptides comprised with the range, particularly, $A\beta_{1-42}$, $A\beta_{1-41}$, $A\beta_{1-40}$, $A\beta_{1-39}$, $A\beta_{1-38}$, $A\beta_{1-28}$, and $A\beta_{1-16}$. A preferred embodiment comprises monoclonal antibody R7CN and compositions of R7CN that react with amyloid proteins and cause a conformational transition in the amyloid protein. A preferred conformational transition is the change from a b-sheet formation of the amyloid protein to an alpha helix form.

A growing body of evidence indicates that $A\beta_{1-42}$ induces apoptotic cell death in cell culture by involving the activation of several caspases (Allen et al., J. Neuroscience Res. Jul. 1, 2000, 65(1):45–53; Troy et al., J. of Neuroscience, Feb. 15, 2000, 20(4):1386–1392). Caspases are a family of cysteine proteases which are theorized to regulate neuronal cell death. In addition, familial Alzheimer's Disease mutations in the amyloid precursor protein and in the presenilin-1/2 genes lead to an increased $A\beta$ production, caspase activation, and enhanced sensitivity to apoptotic cell death (Eckert et al., J. of Neuroscience Research, Apr. 15, 2001, 64(2):183–92; Gervais et al., Cell Apr. 30, 1999, 97(3): 395–406; Wolozin et al., Science, Dec. 6, 1996; 274(5293): 1710–3.) Troy et al., demonstrated that $A\beta_{1-42}$ mediated death in three different types of neuronal cells required the presence of caspases. Furthermore, studies have shown that cellular death induced by $A\beta$ is inhibited by the caspase inhibitor N-benzyloxycarbonyl-val-ala-asp-fluoromethyl ketone.

The compositions of the present invention, comprising monoclonal antibodies which bind to $A\beta$, are effective in preventing neuronal apoptosis and effecting the activity of caspases. In particular, the compositions of the present invention comprising R7CN are effective in preventing neuronal apoptosis and effecting the activity of caspases, and methods for preventing neuronal apoptosis comprise administering an effective amount of compositions comprising R7CN. Other methods of the present invention for treating amyloid-associated disease comprise adminstration of an effective amount of a composition comprising R7CN that effects the activity of caspases.

The present invention comprises compositions comprising monoclonal antibodies that are specific for peptides of .beta.-amyloid, preferably the monoclonal antibodies listed herein in Chart 1 and more preferably, the monoclonal antibody R7CN, deposited with the DSMZ (DSMZ-Deutsche Sammlung von Mikrooganismen und Zellkulturen GmbH, Mascheroder Weg 1b D-38124 Braunschweig, Germany) on Jan. 8, 2003 and assigned Accession No. DSM ACC2581. In general, the methods for making monoclonal antibodies are known in the art. Monoclonal antibodies can be prepared using a wide variety of techniques known in the art including the use of hybridoma, recombinant, phage display technologies, or a combination thereof. For example, monoclonal antibodies can be produced using hybridoma techniques including those known in the art and taught for example, in Harlow et al., Antibodies: A Laboratory Manual, (Cold Spring Harbor Laboratory Press, 2nd ed. 1988). The present invention further comprises the hybridoma cell lines disclosed herein, particularly those cell lines capable of producing the monoclonal antibodies of Chart1, most particularly the hybridoma cell line capable of producing the monoclonal antibody R7CN.

Monoclonal antibodies can (also be generated using various phage display methods known in the art. In phage display methods, functional antibody domains are displayed on the surface of phage particles that carry the polynucleotide sequences encoding them. In a particular embodiment, such phage can be utilized to display antigen binding domains expressed from a repertoire or combinatorial antibody library and can be derived from the immunoglobin genes found in monoclonal antibodies derived from hybridoma techniques. Examples of phage display methods that can be used to make the antibodies include those disclosed in Brinkman et al., J. Immunol. Methods, 182:41–50 (1995); and Ames et al., J. Immunol. Methods 184:177–186 (1995), among others.

Thus, the present invention further comprises the nucleic acids, such as DNA or RNA, or the gene(s) that encode the monoclonal antibodies disclosed herein. In particular, the present invention comprises the gene(s) that encode the monoclonal antibody R7CN, and particularly the antigenic binding site sequences. Such genetic material can be used in gene therapy methods for treating amyloid-associated diseases or for making diagnostic or therapeutic compositions. The gene(s) of the monoclonal antibodies disclosed herein can be used for making humanized monoclonal antibodies having the same reactivities as the originally cloned monoclonal antibodies or in phage display or other methods for making antibody-like binding molecules having the specificity of the monoclonal antibodies disclosed herein.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibody includes antibody-like binding molecules that have the specificity and antigen reactivity that the originally cloned monoclonal antibody made by hybridoma techniques, including, but not limited to, humanized monoclonal antibodies, phage display derived antibodies, and molecules made by gene shuffling or protein rearrangements.

One method for immunizing a mammal, generally a mouse, includes modification of peptides for insertion into liposomes, so that the modified peptides serve as antigens. These antigenic liposomes are used to make monoclonal antibodies from immune cells of the immunized animal using techniques known in the art. In general, the monoclonal antibodies of the present invention were derived from mice immunized with liposomes containing a modified peptide, $A\beta_{1-16}$, to elicit an immune response. Monoclonal antibodies were derived from the fusion of immune cells from the immunized mouse and immortal cells, as generally taught by Kohler and Millstein. The monoclonal antibodies of Chart 1, and a particular monoclonal antibody, R7CN, were developed using this method.

CHART 1

ANTIBODIES AGAINST AB PROTEIN

| No. | Clone Name |
| --- | --- |
| 1. | AN-15E6-A9 |
| 2 | AN-15E6-B9 |
| 3 | AN-15E6-C8 |
| 4 | AN-15E6-C9 |
| 5 | AN-15E6-E8 |
| 6 | AN-6D4-C3 |
| 7 | AN-6D4-D2 |
| 8 | AN-6D4-D1 |
| 9 | AN-6D4-D3 |
| 10 | AN-6D4-D6 |
| 11 | AN-6D4-E1 |
| 12 | AN-6D4-E2 |
| 13 | AN-6D4-E3 |

CHART 1-continued

ANTIBODIES AGAINST AB PROTEIN

| No. | Clone Name |
|---|---|
| 14 | AN-6D4-F1 |
| 15 | AN-6D4-F2 |
| 16 | AN-6D4-F4 |
| 17 | AN-9C2C4-E6 |
| 18 | AN-9C2C4-G6 |
| 19 | AN-9C2C4-G7 |
| 20 | AN-9C2C3-C11 |
| 21 | AN-9C2C3-E4 |
| 22 | AN-9C2C3-G4 |
| 23 | AN-6D4-C1 (R7CN) |

An embodiment of the present invention includes compositions comprising the monoclonal antibody R7CN, which was deposited on Jan. 8, 2003 with the DSMZ (DSMZ-Deutsche Sammlung von Mikrooganismen und Zellkulturen GmbH, Mascheroder Weg 1b D-38124 Braunschweig, Germany)—and assigned Accession No. DSM ACC2581. An embodiment of the present invention comprises methods of detection, diagnosis and treatment of amyloid-associatod diseases using compositions comprising R7CN. Effective amounts of compositions comprising R7CN are administered to humans or animals with amyloid-associated diseases for treatment or prevention of such diseases. The R7CN antibody can be modified as described herein or in known methods, such as by being humanized so that it can be easily administered to humans, or simiiariy altered for administration into the species of interest. Routes of administration of the compositions comprising R7CN include those known and used for pharmaceutical or experimental administration and examples are described here, though preferably, the compositions are administered by intravenous injection. Routes of administration include, but are not limited to, parenteral, subcutaneous, intramuscular, intravenous, intrarticular, intrabronchial, intraabdominal, intracapsular, intracartilaginous, intracavitary, intracelial, intracelebellar, intracerebroveotricular, intracolic, intracervical, intragastric, intrahepatic, intramyocardial, intruosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means.

Compositions comprising monoclonal antibodies specific for Aβ have therapeutic utility in treatment of amyloid-associated diseases, including AD. The compositions are preferably administered to a subject having an amyloid-associated disease, a subject predisposed to developing an amyloid-associated disease, or a subject with a genetic chracteristic linked to amyloid-associated disease development. It will be apparent to those persons skilled in the art that carriers may be used, depending upon, for instance, the route of administration and concentration of the compositions being administered. The compositions can be administered to the subject by injection (e.g., intravenous, intraperitoneal, subcutaneous, intramuscular), or by other methods such as infusion to ensure delivery to the bloodstream is in an effective form. Additional routes of administration, such as those listed above, are included to exert local as well as systemic therapeutic effects.

In a preferred embodiment, the monoclonal antibody or antibody fragment is a humanized antibody. Methods for humanizing non-human antibodies are well known in the art. For examples, see U.S. Pat. Nos. 6,407,213; 6,133,426; and 4,816,567, each of which is incorporated herein in its entirety. Generally, a humanized antibody has one or more amino acid residues introduced into it from a source which is non-human. These non-human amino acid residues are typically taken from a variable domain. It will be appreciated that variable domain sequences obtained from any non-human animal phage display library-derived Fv clone or from any non-human animal hybridoma-derived antibody clone provided as described herein can serve as the variable domain used in the construction of the humanized antibodies of the invention. Humanization can be essentially performed by substituting non-human animal, e.g. rodent, Complementarity Determining Regions, (CDRs) or CDR sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in non-human animal antibodies.

According to one method, the sequence of the variable domain of a non-human animal antibody is screened against the entire library of known human variable-domain sequences. The human sequence which is closest to that of the non-human animal is then accepted as the human framework for the humanized antibody. See U.S. Pat. No. 6,133,426. Another method uses a particular framework derived from the consensus sequence of all human antibodies of a particular subgroup light or heavy chains. The same framework can be used for several different humanized antibodies. It is also important that antibodies be humanized with retention of high affinity for the antigen and other favorable biological properties. To achieve this goal, humanized antibodies may be prepared by analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Analysis of these displays permits determination of the likely role of the residues in the functioning of the candidate immunoglobulin sequence. In this way, framework residues can be selected and combined from the consensus and import sequences so that the desired antibody characteristic, such as increased affinity for the target antigen(s), is achieved. In general, the CDR residues are directly and most substantially involved in influencing antigen binding.

Additionally, it is possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Alternatively, phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. A repertoire of V genes from unimmunized human donors can be constructed and antibodies to a diverse array of antigens (including self-antigens) can be isolated essentially following the techniques. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge.

Gene shuffling can also be used to derive human antibodies from non-human, antibodies, where the human antibody has similar affinities and specificities to the starting non-human antibody. According to this method, either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (See WO 93/06213 published Apr. 1, 1993). Unlike traditional humanization of non-human antibodies by CDR grafting, this technique provides completely human antibodies, which have no framework or CDR residues of non-human origin.

In addition, antibody fragments for use herein can be derived from human monoclonal antibodies. Human monoclonal antibodies against the Aβ peptide can be made by the hybridoma method. Human myeloma and mouse-human heteromyeloma cell lines for the production of human monoclonal antibodies have been described in U.S. Pat. No. 6,133,426, which is specifically incorporated herein in its entirety. DNA, RNA or sequences encoding a particular monoclonal antibody or antibody fragment, or binding sites of interest can be isolated from its hybridoma or phage display clone of origin, and then manipulated to create humanized and/or affinity matured constructs.

In addition, known techniques for modification of proteins can be employed to introduce an amino acid residue or residues into any desired location on the polypeptide backbone of an antibody fragment, e.g. a cysteine residue placed in the hinge region of the heavy chain, thereby providing a site for specific attachment of polymer molecule(s). In one embodiment, the native cysteine residue in either the light or heavy chain of the antibody fragment that would ordinarily form the disulfide bridge linking the light and heavy chains is substituted with another amino acid, such as serine, in order to leave the partner cysteine residue in the opposite chain with a free sulfhydryl for specific attachment of a polymer molecule. See U.S. Pat. No. 6,133,426. Such modifications may be useful in making the monoclonal antibodies resistant to degradation and in providing sustained release compositions. Such modifications can be used to add moieties such as labels or cytotoxic molecules to monoclonal antibody molecules.

The present invention comprises methods for detecting and diagnosing amyloid-associated diseases, and once detected or diagnosed, for treating amyloid-associated diseases. These methods include known immunological methods used for detecting or quantifying substances. Such assays are disclosed for example in U.S. Pat. No. 6,048,526, incorporated herein by referencein its entirety. In particular embodiments of the invention, AD and other amyloid-associated diseases may be diagnosed by detecting the immunospecific binding of a monoclonal antibody or fragment, reactive with an epitope of Aβ in a patient or patient sample. A particular embodiment of the present invention comprises using compositions comprising R7CN for diagnosing the presence of amyloid-associated disease. The patient sample may consist of any body fluid, including but not limited to peripheral blood, plasma, cerebrospinal fluid, lymphatic fluid, peritoneal fluid, or pleural fluid, to name but a few, or any body tissue, particularly neural, cardiac or vascular tissue. Binding may be accomplished and/or detected in vitro or in vivo. In vitro binding may be performed using histologic specimens or subfractions of tissue or fluid. In vivo binding may be achieved by administering the antibody or fragment or derivative compositions by any means known in the art (including but not limited to intravenous, intraperitoneal, intranasal, intracerebral, and intraarterial, to name but a few) such that immunospecific binding may be detected; for example, by attaching a radioactive label to the diagnostic antibody, fragment, or derivative.

In various embodiments, the antibodies, derivatives and fragments thereof of the invention can be used to detect, quantitate, and/or localize Aβ. The antibodies of the invention, and fragments thereof containing the binding region (e.g., Fab, Fab', F(ab').sub.2), can be used in various immunoassays. Such immunoassays include, but are not limited to, competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement fixation assays, immunoradiometric assays, fluorescent immunoassays, protein A immunoassays, and immunoelectrophoresis assays, to name but a few. In addition, imaging techniques can be used, in which an antibody of the invention or derivative or fragment thereof is bound to a label. The labeled antibody can then be administered in vivo to determine the localization of its target antigen. The location of the Aβ detected is compared to a known standard location(s) of Aβ that is indicative of amyloid-associated diseases.

For example, a capture-ELISA (CELISA) may also be used for diagnosis of amyloid-associated diseases. The CELISA comprises: a) coating the monoclonal antibody reactive with Aβ onto a surface, b) adding a sample containing an unknown amount of Aβ or a standard concentration of purified Aβ to the surface, c)adding a monoclonal antibody of the invention that binds to Aβ at the same or different epitopes, adding an enzyme-linked tertiary antibody (reactive to the monoclonal added in c)), and determining the presence of Aβ by quantifying the amount of enzymatic label present in a colorimetric reaction. The amount Aβ detected is compared to a known standard amount of Aβ that is indicative of amyloid-associated diseases.

The present invention also relates to a diagnostic kit for use in detecting the presence of Aβ in a biological sample, based, on the method described above. In one embodiment, the diagnostic kit comprises (i) the monoclonal antibody or antibodies (or binding fragment(s) thereof) as defined above, and (ii) a conjugate of a specific binding partner for the monoclonal antibody and a label capable of producing a detectable signal. Reagents, such as ancillary agents, buffering agents, protein stabilizing agents and the like, can also be included. The diagnostic kit can further include: other members of the signal producing system, of which system the label is a member, agents for reducing background interference in a test, control reagents, and apparatus for conducting a test. In another embodiment, the diagnostic kit comprises a conjugate of a monoclonal antibody or antibodies of the invention and a label capable of producing a detectable signal, a container and packaging.

The methods of the present invention are particularly useful for persons who are most at risk for developing amyloid-associated disease. For example, there are well known genetic relationships that predispose persons to develop AD at a later time. The polymorphic allele of apolipoprotein E, ε4, on chromosome 19 was identified as a major susceptibility gene in late-onset AD. The gene, ε4, increases the risk of developing AD in a gene-dosage dependent manner. There are also inheritable forms of AD, such as autosomal dominantly inherited familial AD, FAD. The methods of the present invention for preventing the on-set of amyloid-associated disease comprise identifying persons with predisposition of developing AD, such as those humans or animals having these or other genetic chracteristics or traits, and treating them with compositions comprising monoclonal antibodies that bind or are reactive with Aβ. The antibodies that are useful for detecting, diagnosing and treating amyloid-associated disease include those antibodies that bind or are reactive with amyloid peptides comprising a range of about $A\beta_1$ to $A\beta_{1-42}$, and all peptides comprised with the range, particularly, $A\beta_{1-42}$, $A\beta_{1-41}$, $A\beta_{1-40}$, $A\beta_{1-39}$, $A\beta_{1-38}$, $A\beta_{1-28}$, and $A\beta_{1-16}$.

In particular, the methods for preventing amyloid-associated disease comprise administering to a person having genetic traits associated with amyloid-associated disease, an effective amount of a composition comprising R7CN. Additionally, the present invention comprises methods of treating persons who show genetic or physiological conditions associated with amyloid-associated diseases. For example, for persons who are presently diagnosed with early dementia, where AD is suspected as the cause of the dementia, the methods of treating a person with an amyloid-associated disease comprising administering an effective amount of a composition comprising an antibody that binds to or is reaction with Aβ, in particular, administering an effective amount of a composition comprising R7CN. Furthermore, the methods of the present invention comprise restoring memory function to a human or animal by administering an effective amount of a composition comprising an antibody that binds to or is reactive with Aβ, particularly administering an effective amount of a composition comprising R7CN.

The present invention also comprises methods and compositions comprising a fusion protein. The fusion protein comprises 1) at least one segment of a binding region which binds to an epitope or fragment, preferably an epitope such as one located in β-amyloid and 2) one or more segments comprising portions, fragments or whole proteins having a desired function. The segment comprising the binding region can be any binding partner that is capable of attaching, binding or associating with an amyloid-associated moiety. For example, the variable region of an antibody, including the light or heavy chain or both, can be the binding region that is capable of binding an epitope found on an Aβ protein. In a particular aspect of the invention, the variable region of the R7CN mAb is sequenced and the sequences are joined with the sequences of a molecule having a desired function, such as ability to transverse cellular membranes. The fusion proteins retain the property of the antibody R7CN to solubilize β-amyloid fibers. Incorporation of genes or other nucleic acid segments, such as coding regions, into expression vectors can be effected using methods known to the skilled artisan. In this context, reference can be made to the textbooks of Maniatis et al. (*Molecular Cloning*, Cold Spring Harbor Laboratory, 1982) and Sambrook et al. (*Molecular Cloning-A Laboratory Manual*, 2nd. ed., Cold Spring Harbor Laboratory, 1989), the contents of both being herein incorporated by reference. Fusion proteins can also be made by chemical means for joining proteins or peptides.

This invention also provides for pharmaceutical compositions comprising monoclonal antibodies capable of binding to Aβ or antigens associated with amyloid-associated diseases together with suitable diluents, preservatives, solubilizers, emulsifiers, adjuvants and/or carriers. Such compositions can be liquids or can be lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol). The compositions may further comprise monoclonal antibodies of the present invention having covalent attachment of polymers such as polyethylene glycol, complexation with metal ions, or incorporation of the compositions into or onto particulate preparations of polymeric compounds such as polylactic acid, polglycolic acid, hydrogels, or into liposomes, microemulsions, micelles, unilamellar or multilamellar vesicles, erythrocyte ghosts, or spheroplasts. Such compositions influence the physical state, solubility, stability, rate of in vivo release, and rate of in vivo clearance of the monoclonal antibody or the composition.

Controlled or sustained release compositions of the present invention include formulation in lipophilic depots (e.g., fatty acids, waxes, oils). Other embodiments of the compositions of the invention incorporate particulate forms protective coatings, protease inhibitors or permeation enhancers for various routes of administration, including parenteral, pulmonary, nasal and oral.

When administered, compositions are often cleared rapidly from the circulation and may therefore have relatively short-lived pharmacological activity. Consequently, frequent injections of relatively large doses of bioactive compounds may by required to sustain therapeutic efficacy. Antibodies modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline may exhibit substantially longer half-lives in blood following intravenous injection than do the corresponding unmodified antibodies (Abuchowski et al., Cancer Treat. Rep. November–December; 65(11–12): 1077–81

(1981); and Katre et al., PNAS USA 84(6):1487–91 (1987)). Such modifications may also be used increase the antibodies' solubility in aqueous solution, eliminate aggregation, enhance the physical and chemical stability of the antibodies. As a result, the desired in vivo biological activity may be achieved by the administration of such polymer-antibody compositions less frequently or in lower doses than with the unmodified antibody.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Effective dosages and administration methods for delivery of the compositions comprising monoclonal antibodies may be determined empirically and such determinations are within the skill of an artisan. Those skilled in the art will understand that the dosage required depends on the subject receiving the composition, the route of administration and other substances being administered, among other considerations. The antibodies of the invention may be administered systemically by intravenous or peritoneal perfusion, or by bolus injection into the subcutaneous tissue or muscle. The antibodies may be delivered in vehicles generally known to those skilled in the art, such as saline, balanced salt solutions, isotonic or phosphate buffered saline (pH 7), with or without dextrose. An effective amount of antibody administered may be measured by maintaining the circulating serum concentration from about 0.0001 μg to 5 mg per mL serum, from about 0.001 μg to 4.5 mg per mL, from about 0.01 μg to 4.0 mg per mL, from about 0.01 μg to 2.0 mg per mL, from about 0.1 μg to 1.0 mg per mL, from about 0.0001 μg to 1.0 mg per mL, and from about 0.01 μg to 5.0 mg per mL, and all amounts comprised therein.

The compositions of the present invention may also be administered in combination with effective amounts of one or more other therapeutic agents, either in separate compositions or combined into one composition. The compositions may be administered sequentially or concurrently with the one or more other therapeutic agents. The amounts of antibody compositions and therapeutic agent compositions depend on the type of therapeutic agents are used, the condition being treated, and the scheduling and routes of administration, among other considerations. For example, therapeutic agents that have been used in treatment of amyloid-associated disease, such as AD, include, but are not limited to cholinesterase inhibitors including donepezil, rivastigiine, galantamine, tacrine; vitamins and minerals; antipsychotic drugs including risperidone, olanzapine, quetiapine, haloperidol, fluphenazine, thiothixene, trifluroperazine, molindone, perphenazine, loxapine; mood-stabilizing drugs such as trazadone, carbamazepine, divalproex sodium; anxiolytic drugs, benzodiazepines, lorazepam, oxazepam, temazepam, zolpidem, triazolam; nonbenzodiazepines, buspirone; antidepressant drugs including tricyclic antidepressant agents; SSRI including fluoxetine, paroxetine, sertraline, citalopram, fluvoxamine, phenethylamine, venlafaxine, lithium; statins and antioxidants. The therapeutic agents are contemplated in the compositions of the present invention, whether given in a separate composition or in combination with the monoclonal antibodies of the present invention.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention which will be limited only by the appended claims.

As used herein and in the appended claims, the singular forms "a," "an," and "the" include plural reference unless the context clearly indicates otherwise. Thus, for example, reference to an "antibody" is a reference to many antibodies, such as molar amounts, and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The invention set forth above has been described with regard to specific examples and general description. Alterations therefrom, particularly with regard to carrier type, dosage range, etc., will not depart from the invention. Further, the invention has been extensively described and illustrated with regard to discussion of specific monoclonal antibody strains. Minor modification of the antibody, the cell line expressing the antibody, etc., without effecting the basic neutralizing or binding characteristics of those monoclonal antibodies, is within the skill of those in the art, and does not depart from the scope of the invention.

The following describes methods for making and using monoclonal antibodies. It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

EXAMPLES

Example 1

Preparation of $A\beta_{1-16}$ Antigen

A first step in making an antigenic component comprises synthesis of tetrapalmitoyl-tetrakis-lysine-$A\beta_{1-16}$-peptide. Two sequential ε-palmitoylated lysines were introduced at the peptide's C-terminus. The first ε-palmitoylated lysine was anchored onto the 4-alkoxylbenzyl alcohol resin by reacting 335 mg of resin with 388 mg of FmocLys(Pal)OH in the presence of DCC (185 mg) and DMAP (20 mg) in dry, freshly distilled dichloromethane according to Merrifield Lu, G., Mojsov, S., Tam, J. P. & Merrified, R. B. (1981) J. Org. Chem. 46, 3433–3436.

After stirring for three hours at room temperature, the reaction mixture was filtered and thoroughly washed ten times with dry methylene chloride. In order to ensure a complete reaction, the obtained resin was reacted a second time with a fresh portion of FmocLys(Pal)OH, in the presence of DCC and DMAP in dry methylene chloride. The resin was then suspended in 45 ml dry methylene chloride and 5 ml acetic anhydride was added for capping any unreacted resin. After washing with methylene chloride the resin was dried in vacuum.

The second ε-palmitoylated lysine was anchored on the peptide synthesizer also employed for coupling FmocLys (Pal)OH. Subsequently, 16 cycles of conventional automated solid phase peptide synthesis were performed resulting in the sequence $A\beta_{1-16}$ appended to the first two palmitoylated lysines. At this point, a small amount of peptide was cleaved from the resin and analyzed by electrospray mass spectrometry (ES-MS) and HPLC showing that in addition to the desired lipopeptide, minor components of peptides lacking either one or two palmitoylated lysines were also present.

Two further couplings, each repeated twice, were effected with fluorenylmethoxycarbonyl (Fmoc) protected ε-palmitoyllysine (Fmoc-Lys(Pal)-OH). Final deprotection and cleavage from the resin afforded a mixture of lipopeptides.

Liposomes with Lipid A were used as adjuvants to prepare the amyloid antigen. See Tosi, P.-F., Radu, D. & Nicolau, C. (1995) Biochem. Biophys. Res. Com. 212, 494–500. Dimyristoylphosphatidyl-choline, dimyristoyl-phosphatidyl-glycerol, and cholesterol were mixed in molar ratios of 0.9:0.1:0.7. Monophosphoryl lipid A, a strong immunomodulator, was added at a concentration of 40 mg per mmnol of phospholipids. The palmitoylated peptides were added at a molar ratio peptide to phospholipids of 1:100. Solvents were evaporated and the resultant film was hydrated with sterile PBS (pH 7.3) to a final phospholipid concentration of 4 mmol which was further homogenized. The liposome suspension was mixed with sterile Alum, 15 minutes before injection (9:1 vol:vol).

Example 2

Preparation of Monoclonal Antibodies to $A\beta_{1-16}$

Using tetrapalmitoyl-tetrakis-lysine-$A\beta_{1-16}$ reconstituted in liposomes with lipid A as an antigen, as made above in Example 1, C57B1/6 mice were inoculated i.p. The mice received 5 immunizations over a period of 10 weeks and anti-amyloid antibodies of 1:5000–1:10,000 were measured by ELISA at the end of this interval. See Schenk et al., Nature (London) 400, 173–177 (1999).

The mice were tested using the ELISA described below for reaction to synthetic $A\beta_{1-42}$ fibers. Synthetic, human $A\beta_{1-42}$ sequence was incubated for seven days in PBS at pH=7.3. This resulted in the formation of fibers, which bind Thioflavin-T, a fluorescent dye emitting at 482 nm.

To perform the ELISA, microtiter plates were coated with 50 μl of $A\beta_{1-42}$ solution (1 mg $A\beta_{1-42}$/5 ml PBS) and left overnight at 4° C. Wells were blocked with 200 μl BSA/PBS (0.5% BSA) for two hours at 37° C. and washed with 200 μl of PBS/0.005% Triton X-100. Dilutions of sera (1:10–1:100,000) were incubated for 90 min at 37° C. The plates were then washed twice with 200 μl of PBS/0.005% Triton X-100 before 50 μl of a goat-anti-mouse antibody (alkaline phosphatase conjugated) was added in a 1:30,000 dilution. After 90 min at 37° C., the wells were washed as described. 100 μl of the paranitrophenyl phosphate substrate (PNPP, 1 tablet in 5 ml deionized water), were added and optical absorption was measured at 405 nm in an ELISA reader after 20–60 min. Frenkel, D., Katz, O. & Solomon, B. (2000) PNAS USA 97, 11455–11459.

Reaction tubes containing 30 μg $A\beta_{1-42}$/10 μl PBS, pH 7.3 were incubated for 1 week at 37° C. Aggregation was measured by the Thioflavin T (ThT) binding assay in which the dye's fluorescence emission intensity reflects the degree of Aβ fibrillar aggregation. Disaggregation was followed after addition of various undiluted sera of immunized mice (or after addition of 5–20 μl of supernatants obtained from hybridomas) to the preformed fibers (10 μl each). The reaction mixtures were incubated for 2 days at 37° C. The mAb, 6C6, and an irrelevant control antibody (mouse IgG, anti-$His_5$) were used at a final concentration of 0.4–3.5 mg/ml. The fluorescence (em.: 450 nm, ex.: 482 nm) was measured after addition of 1 ml of ThT (3 μM in 50 mM sodium phosphate buffer, pH 6.0). See Baumeister, R. D. & Eimer, S. (1998) Angew. Chem. Int. Ed. 37, 2978–2982.

Using an ELISA, a significant immune response to liposomes/$A\beta_{1-16}$ vaccinated C57B1/6 mice was observed after the third inoculation. The sera reached titres up to 1:10,000 against $A\beta_{1-42}$. No antibodies against $A\beta_{1-42}$ were found in sera from mice having received scrambled $A\beta_{42-1}$, or lipids only.

Disaggregation of $A\beta_{1-42}$ fibrils was seen when antisera of the vaccinated mice showing titers of at least 1:5,000 were tested for their capacity to solubilize preformed $A\beta_{1-42}$ fibers. A disaggregation assay of $A\beta_{1-42}$ aggregates was performed as described by Solomon, B., Koppel, R., Frankel, D. & Hanan-Aharon, E. (1997) PNAS USA 94, 109–112. A significant solubilization of $A\beta_{1-42}$ fibers by 15 different antisera was observed after an incubation time of two days. The irrelevant mAb had no significantt effect on the disaggregation of the $A\beta_{1-42}$ fibers.

After the $5^{th}$ inoculation, the mice were sacrificed and spleen cells were collected. Spleen cells and cells of the myeloma cell line SP2/0 were mixed in a 5:1 ratio and centrifuged. The pellet was incubated for 90 sec with PEG-solution 50% (Sigma) and later diluted with DMEM medium. After 5 min the cell suspension was centrifuiged (160×g for 5 min, RT). Cells were incubated in 96 well plates with DMEM+10% FCS, penicillin, streptomycin and HAT-supplement (Hypoxanthin, Aminopterin and Thymidin) for 2 weeks. Supernatants were tested for specific antibodies in an ELISA as described, before the cells of single wells were subcloned twice. Subclones were incubated in medium without FCS before their supernatants were used in disaggregation assays.

Example 3

Measurement of Binding to $A\beta_{1-42}$

ELISAs were performed with supernatants of hybridomas from three selected populations (AN-15E6, AN6D4 and AN9C2). The supernatants from these populations showed a significant binding to $A\beta_{1-42}$ in the assay, and the capability of solubilizing $A\beta_{1-42}$ fibers in vitro. Subclones were obtained and tested for specific antibodies in an ELISA. The ELISA values of the supernatants of these clones at $OD_{405}$ are listed in Table 1.

TABLE 1

ELISA Response of the Supernatants of Hybridoma Subclones

| No. | Clone Name | ELISA [OD$_{405}$] |
|---|---|---|
| 2 | AN-15E6-A9 | 0.117 |
| 3 | AN-15E6-B9 | 0.118 |
| 4 | AN-15E6-C8 | 0.159 |
| 5 | AN-15E6-C9 | 0.128 |
| 6 | AN-15E6-E8 | 0.112 |
| 7 | AN-6D4-C1* | 0.339 |
| 8 | AN-6D4-C3 | 0.298 |
| 9 | AN-6D4-D2 | 0.392 |
| 10 | AN-6D4-D1 | 0.373 |
| 11 | AN-6D4-D3 | 0.241 |
| 12 | AN-6D4-D6 | 0.365 |
| 13 | AN-6D4-E1 | 0.182 |
| 14 | AN-6D4-E2 | 0.194 |
| 15 | AN-6D4-E3 | 0.386 |
| 16 | AN-6D4-F1 | 0.366 |
| 17 | AN-6D4-F2 | 0.375 |
| 18 | AN-6D4-F4 | 0.373 |
| 19 | AN-9C2C4-E6 | 0.143 |
| 20 | AN-9C2C4-G6 | 0.365 |
| 21 | AN-9C2C4-G7 | 0.2 |
| 22 | AN-9C2C3-C11 | 0.166 |
| 23 | AN-9C2C3-E4 | 0.101 |
| 24 | AN-9C2C3-G4 | 0.168 |
| Controls | | |
| DMEM/10% FCS | | 0.124 |
| DMEM/10% FCS/2% HCF | | 0.113 |
| serum free Medium | | 0.147 |
| irrelvant mAb | | 0.02 |

*R7CN monoclonal antibody

Example 4

Characterizing the Monoclonal Antibodies Solubilize Aβ$_{1-42}$

R7CN and the other subclones were tested for their ability to disaggregate preformed β-amyloid fibers. The reaction mixtures containing 30 μg Aβ$_{1-42}$/10 μl PBS were incubated for 1 to 2 days with 20 μl of some selected supernatants of hybridomas.

Supernatants of the subclones were tested for their capacity to solubilize Aβ$_{1-42}$ fibers. The results are shown in FIG. 1. As controls, Aβ only was incubated. There was no significant difference between the amount of Aβ fibers in the control.

ThT fluorescence emission intensity correlates with the amount of fibrillar amyloid present in solution. FIG. 1 shows Aβ fiber formation during 8 days at 37° C. in PBS, pH=7.1. 10 μl of the supernatants were added after 7 days and incubated for 24 hr. Bar #1: Aβ without supernatant, Bars #2–24: Aβ+supernatant of clone No. 2–24 (see Tab. 1.), Bar #25: Aβ+serum free medium.

Example 5

Determination of the Size of Particles

To determine the size of particles in the reaction mixtures containing Aβ$_{1-42}$ only, Aβ$_{1-42}$ and hybridoma supernatant ± protease inhibitor samples were measured in an elastic light scatter (Malvern Instruments, S.A., Orsay CEDEX, France). Particles with a size of >5 nm and <5 μm can be detected by this device. Five measurements per sample diluted in 1 ml PBS (pH 7.2) were performed with the wavelength of 633 nm, (Refraction index) R$_1$=1.34.

Figure 2A:
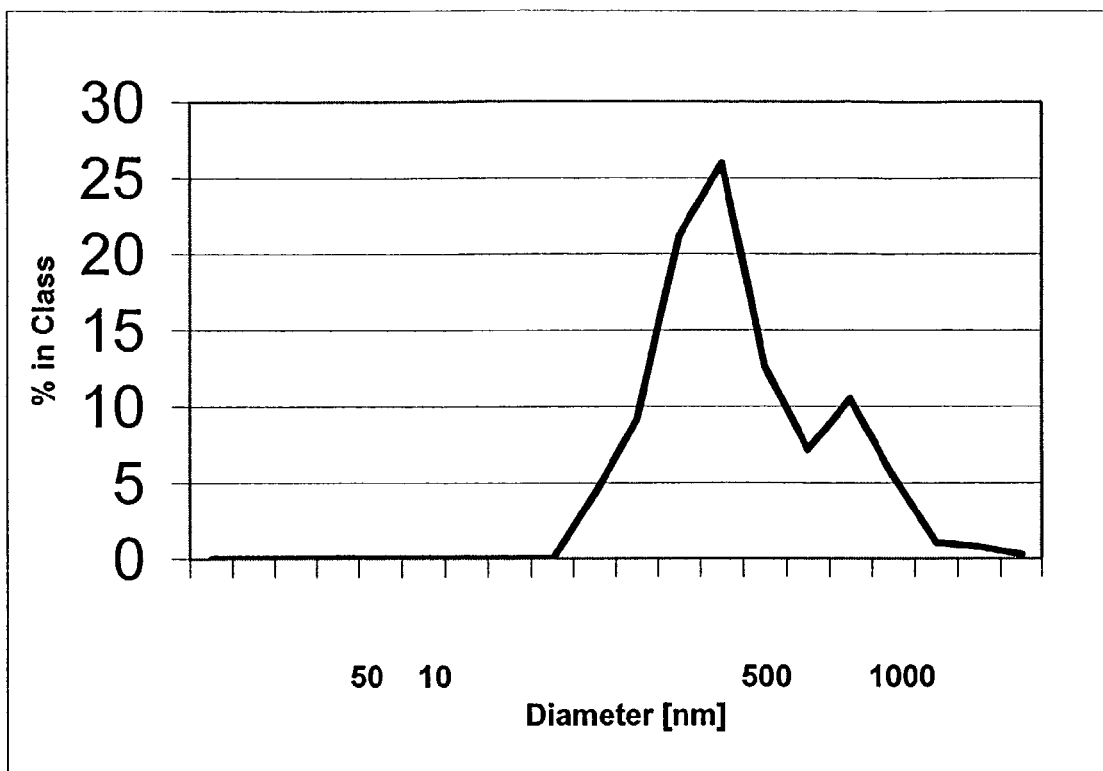
FIGS. 2A and B are charts showing size distribution of $A\beta$ aggregates after incubation with the supernatant of clone R7CN (A) for 24 h, and the supernatant only (B).
Figure 2B:
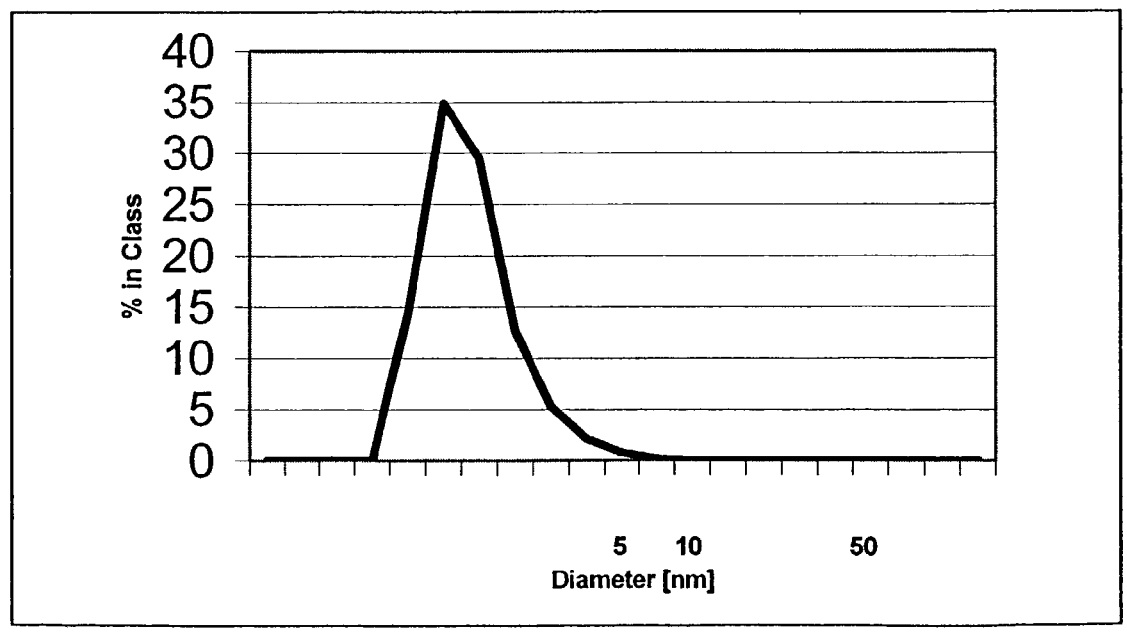

Measurements were taken of the following samples: Aβ$_{1-42}$ only, incubated for 7 days; Aβ$_{1-42}$ and R7CN, added on day 6; and Aβ$_{1-42}$ and hybridoma supernatant of clone R7CN+EGTA, both added on day 6. Supernatant alone and PBS were used as controls. The results are shown in Table 2 and FIG. 2.

TABLE 2

Measurements of the Size of Aβ-Aggregates after Incubation with Hybridoma Supernatants Using Elastic Light Scatter

| Sample | Size |
|---|---|
| Aβ only | >10 μm (100%) |
| Aβ + SN | 470 nm (61%) |
| SN only | 2.7 nm |
| Aβ + SN + EGTA | >10 μm (100%) |
| PBS only | no signal |

SN = supernatant (10 μl/sample),
AB = Beta Amyloid (30 μg/μl),
concentration of EGTA was 5 mM,
amyloid was incubated for 7 days, supernatants and inhibitors were added on day 6

Means of five measurements per sample diluted in 1 ml PBS (pH 7.3) were performed with the wavelength of 633 nm, (Refraction index) R$_1$=1.34. (A) gave a peak: mean 465.1 nm, width 206.3, 61% in range; (B): gave a peak: mean 2.7 nm, width 1.1, 38.5% in range. The samples containing Aβ only and Aβ+supernatant+EGTA generated particles larger than 5 μm and was therefore not detectable by the elastic light scatter. The size of particles in these samples were estimated as more than 10 μm. The addition of the monoclonal antibody R7CN to the fiber suspension at a w/w ratio mAb : Aβ$_{1-42}$ of 1:100 and incubation for 24 hrs under the same conditions resulted in 61% of Aβ$_{1-42}$ to have sizes of about 470 nm. (Table 2). This dramatic change of size induced by the mAb as a result of its direct interaction with the Aβ$_{1-42}$ aggregates suggested that solubilization of the fibers might be due to a conformational change in the aggregates, from β-sheet to α-helix.

Samples containing Aβ$_{1-42}$ in the concentration described above were incubated with antibodies of R7CN for 1 or 2 days. To some samples the inhibitor was also added and the sample was incubated for 1 or 2 days. Control samples contained amyloid only, supernatant of clone R7CN only, and amyloid+EGTA.

Figure 3:
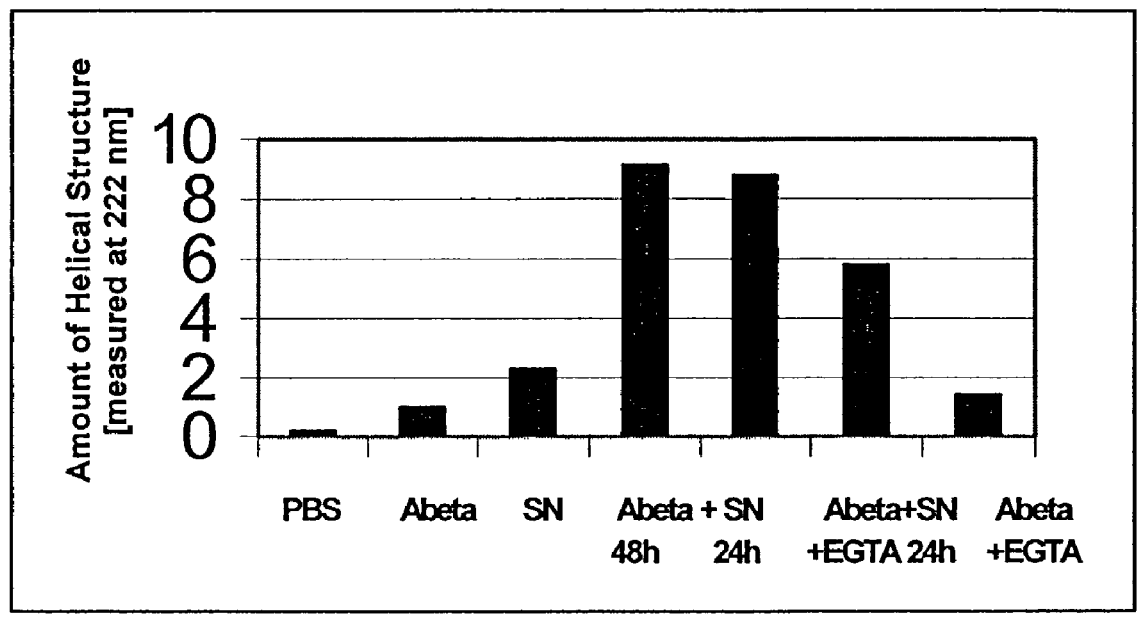
FIG. 3 is a chart showing the increase in the amount of amyloid $\beta$ present in $\alpha$-helix-conformation after incubation with the supernatant of clone R7CN.

Samples of Aβ fibers incubated with the monoclonal antibodies for one or two days were assayed for increasing amount of α-helical conformation of the protein. There was a significant increase of amyloid in α-helix-conformation after incubation with the monoclonal antibodies. The results are depicted in FIG. 3. Samples containing 120 μM Aβ fibers incubated with 80 μl of the supernatant (SN) of clone R7CN for 24 or 48 h. As controls, buffer (PBS), Aβ fibers only and supernatant only were measured (first 3 bars). The effect of the inhibitor EGTA on the solubilizing effect of the antibody, or on amyloid only is shown in the last 2 bars. The means of 5 measurements are given.

Figure 4:
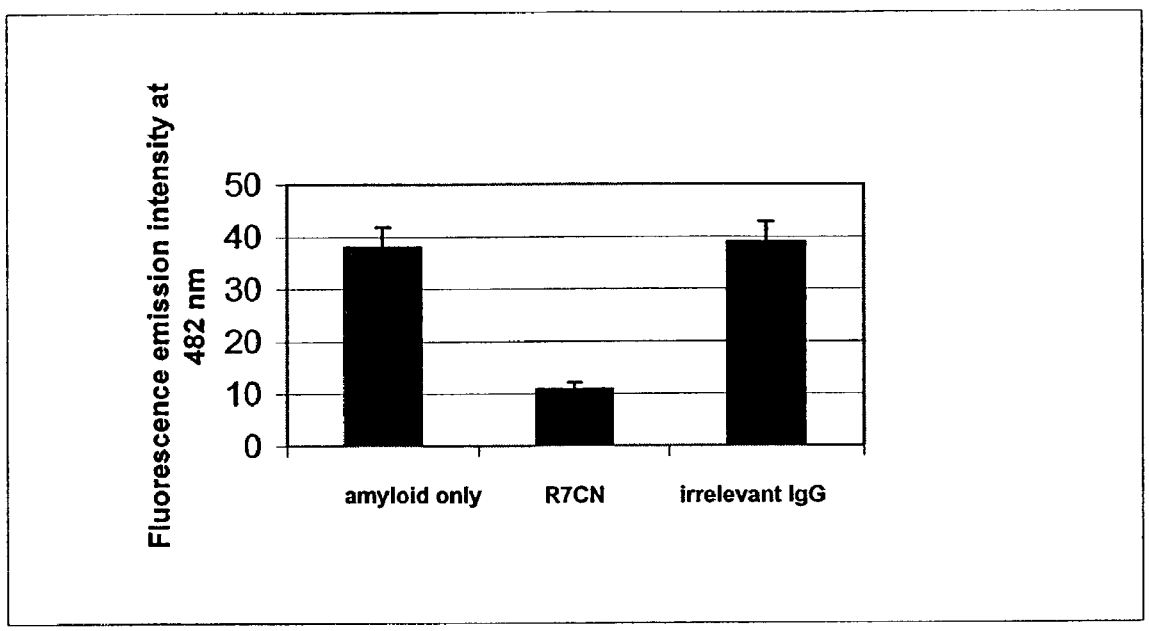
FIG. 4 is a chart showing disaggregation of $A\beta_{1-42}$ by the monoclonal antibody R7CN.

Addition of the R7CN mAb to the fluorescence-labeled Aβ$_{1-42}$ fibers and incubation of the mixture for 24 hrs at 37° C. resulted in extensive solubilization of the fibres as evidenced by decrease in the intensity of fluorescence emission of bound ThT. About 75% of the intensity of emission of ThT is lost as a result of the interaction of the fiber with the mAb. Incubation of the labeled fibers, with an irrelevant IgG under the same conditions had no effect on the intensity of the fluorescence emission of bound ThT (FIG. 4). Similar results were obtained when the fluorescence-labeled $A\beta_{1-42}$ fibers were incubated with the antisera of 15 mice, immunized with tetrapalmitoylated $A\beta_{1-16}$ reconstituted in liposomes-lipid A.

Example 6

Kinetic Study of Changes in Conformation Using Circular Dichroism Spectroscopy (CD)

Figure 5:
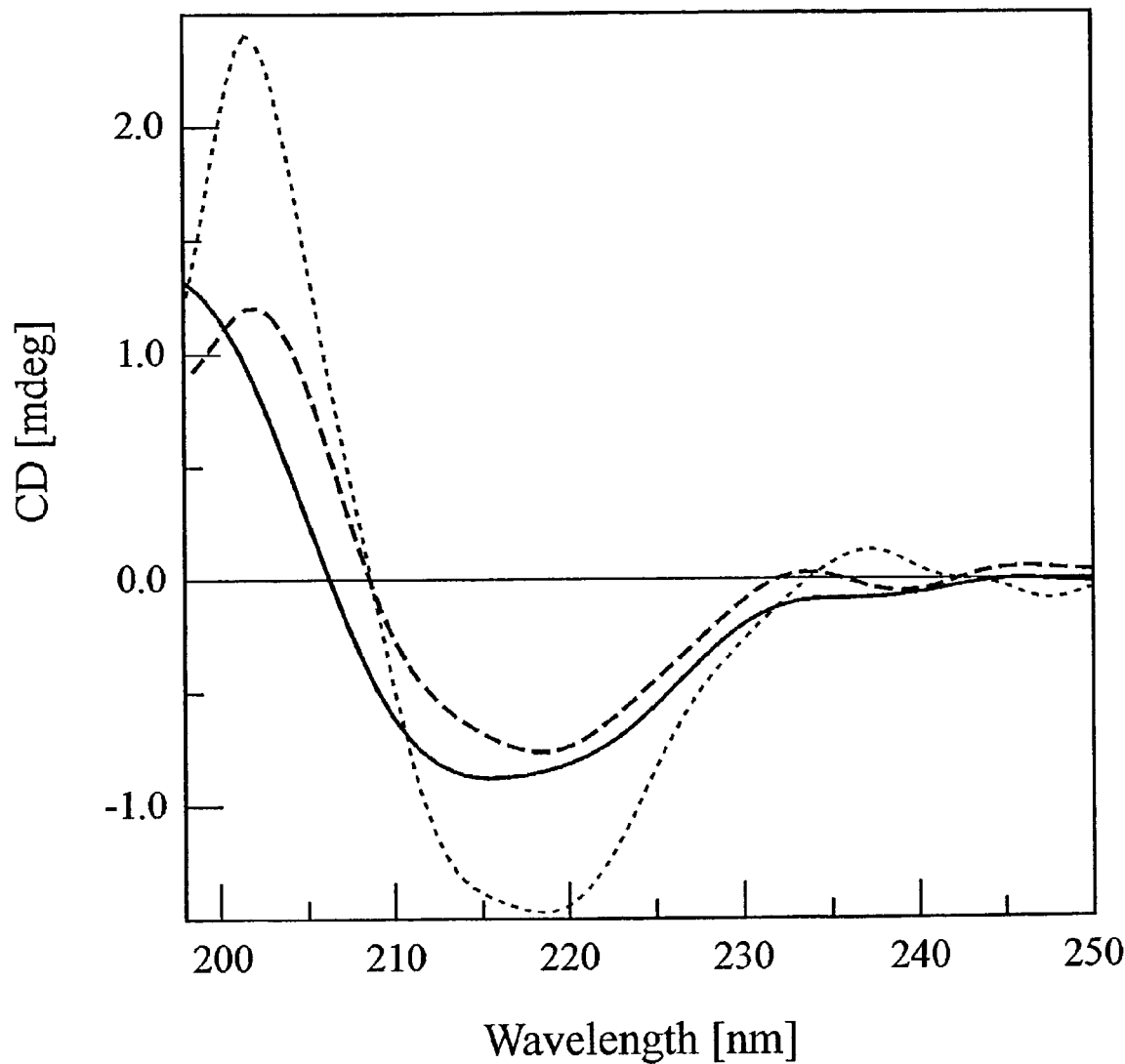
FIG. 5 is a graph of the results of CD measuring conformational changes induced in the $A\beta_{1-42}$ fiber after incubation with R7CN.

Attempts to measure directly the effect of the antibodies on $A\beta_{1-42}$ fibers were strongly affected by light scattering. An indirect approach was therefore used, examining the supernatant containing soluble amyloid after centrifugation of the mixture ($A\beta_{1-42}$ fibers 0.5 mg/ml: R7CN mAb 0.25 mg/ml. To determine the amount of protein in the α-helix conformation, samples underwent a measurement by a CD (spectropolarimeter, J-710, JASCO, Gross-Umstadt, Germany), which detects the amount of α-helical structure in a protein solution at an excitation wavelength of 222 nm. Five spectra were taken with the following parameters: excitation: 200 nm–250 nm, 0.1 nm steps. The amyloid samples were diluted in 550 µl PBS (pH 7.2) so that the molarity of amyloid was approximately 120 µM. The measurements were performed in quartz cuvettes at 20° C. In a control experiment, in the absence of antibodies, all fibers sedimented at 5800×g and no protein was detectable in the CD spectrum. In the sample containing antibodies, the CD spectrum of a pure antibody solution was obtained at t=0 (FIG. 5, dotted line). The spectrum represented 75% of the antibodies present in the mixture, indicating that 25% of R7CN was bound to the fibers, under the experimental conditions used. After 7 days of incubation, only 45% of the antibodies present at t=0 could be detected (FIG. 5, dashed line). The fraction of R7CN bound to the amyloid fibers thus increased to 55%. After 9 days of incubation, the negative CD signal at 218 nm in the spectrum of the supernatant started to shift to a lower wave-length. This shift is even more apparent after 12 days of incubation (FIG. 5, solid line). The shift observed in the negative CD signal with this mixture is opposite to that observed during the polymerization of amyloid. Numerical analysis using several algorithms indicated an increase of α-helix content and a decrease of β-sheet content, which is the opposite of what is observed during polymerization of amyloid. No change was observed in the CD spectra of either pure R7CN incubated for 12 days without $A\beta_{1-42}$ fibers or in the fibers over the same period of time.

Example 7

Mass Spectroscopy Study

Figure 6:
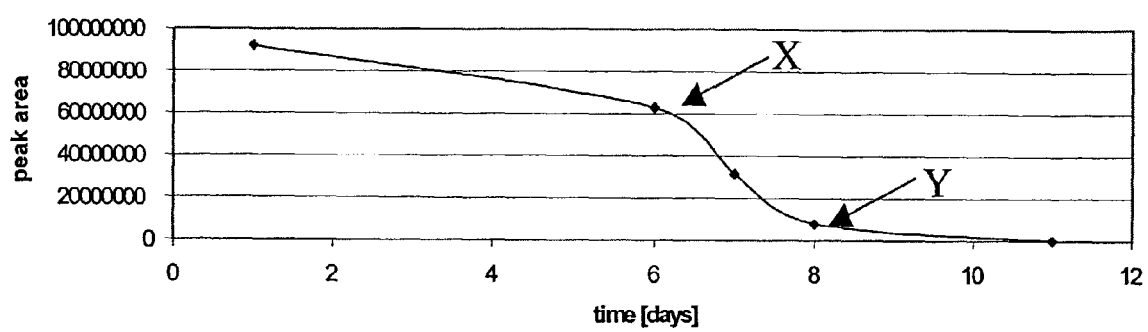
FIG. 6 is a graph of the results of a MS-LC study with the results at day 6 (X) and day 8(Y) indicated.
Figure 7A:
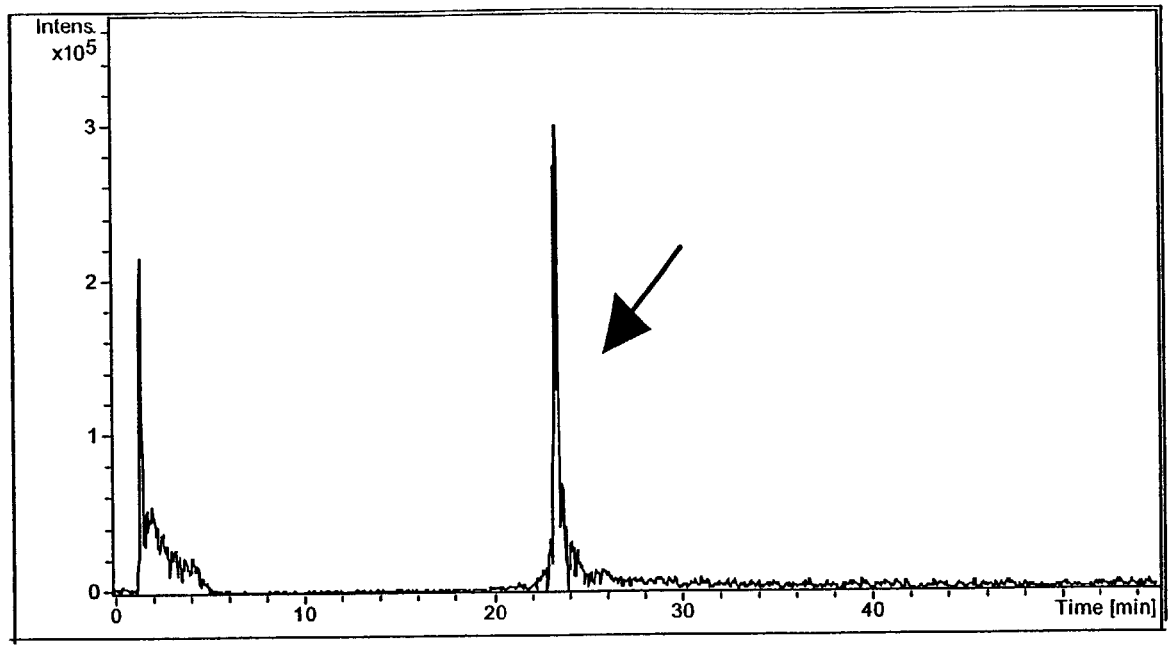
FIG. 7A is a graph of an extracted ion chromatogram of $A\beta_{1-42}$ at day 6, with peak 1 indicating $[M+4H]^{4+}$ and peak 2 indicating $[M+3H]^{3+}$.
Figure 7B:
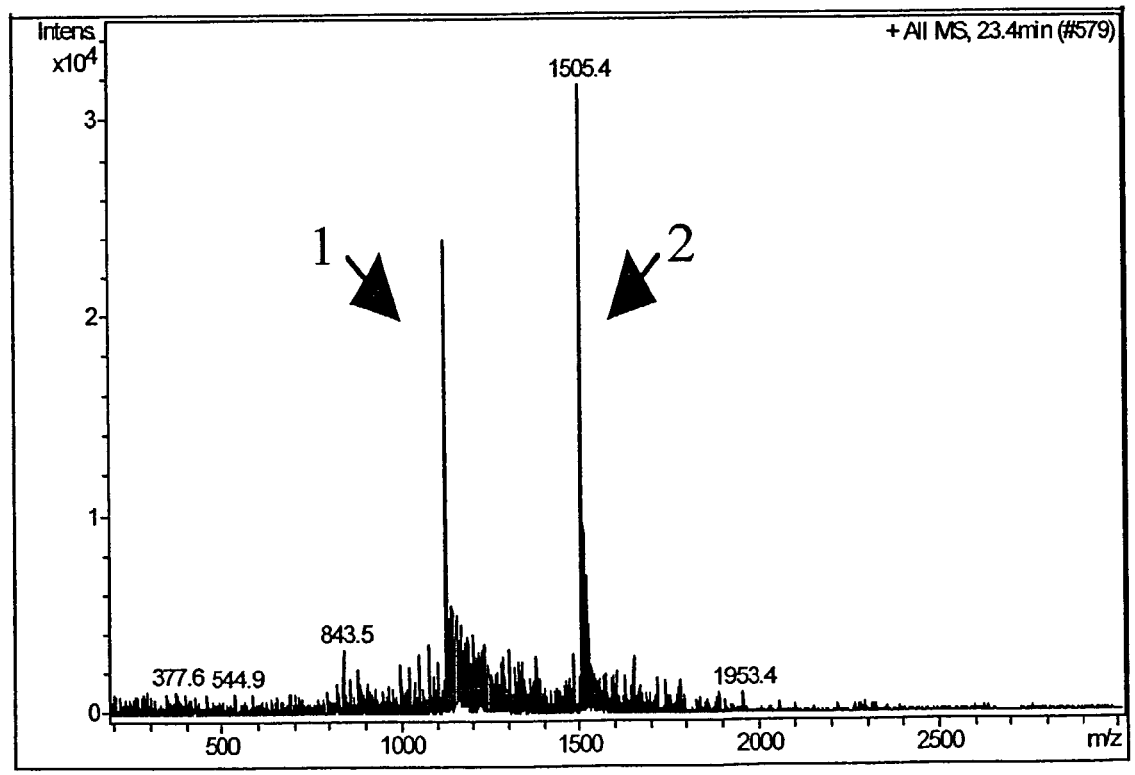
FIG. 7B is a graph of a mass spectrograph of $A\beta_{1-42}$ at day 6.
Figure 8A:
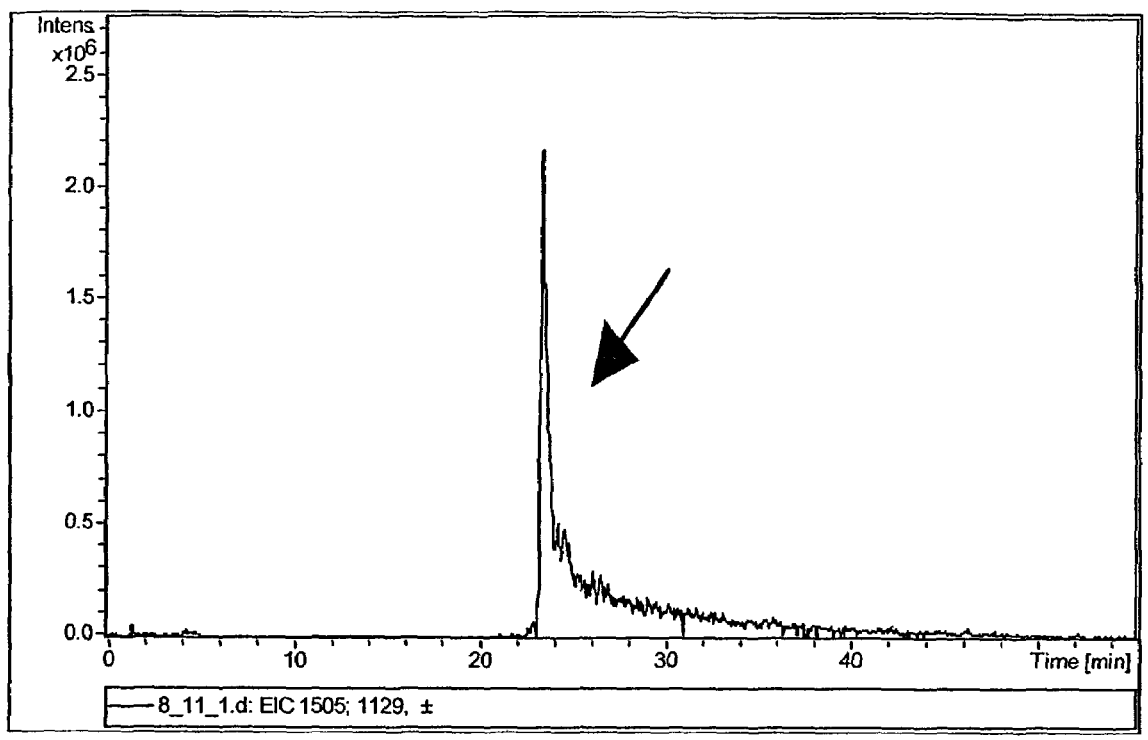
FIG. 8A is graph of an extracted ion chromatogram of $A\beta_{1-42}$ at day 8, with peak 1 indicating $[M+4H]^{4+}$ and peak 2 indicating $[M+3H]^{3+}$.
Figure 8:
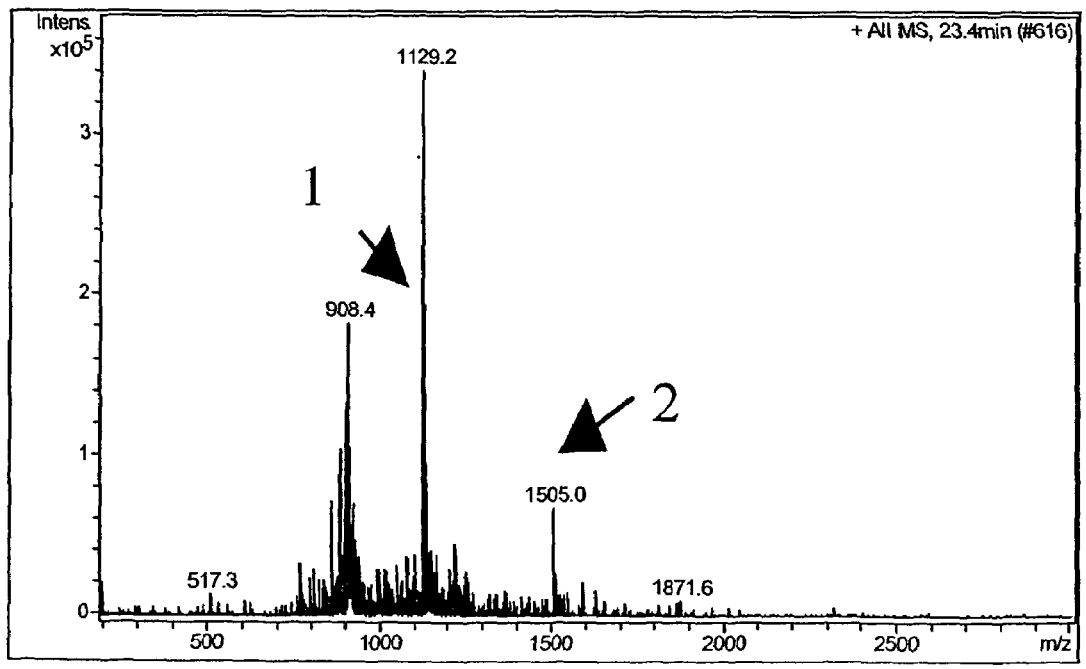
FIG. 8B is a graph of a mass spectrograph of $A\beta_{1-42}$ at day 8.

Decrease of the peak area of a $4.4\times10^{-5}$ M $A\beta_{1-42}$ solution (about 0.4 mg $A\beta_{1-42}$ were dissolved in 200 µl PBS buffer and afterwards diluted 1:10 in PBS buffer), which was incubated at 37° C. for several days. At different times 5 µl were injected in the HPLC-MS system. After 11 days no $A\beta_{1-42}$ could be detected (determination limit S/N: 10/1). As can be seen in FIG. 6, a MS-LC study indicates that $A\beta_{1-42}$ is fully polymerized after 11 days in PBS at pH=7.3. Neither mass spectrometry, nor liquid chromatography could detect any $A\beta_{1-42}$ "monomer" at this time point. Incubation with the monoclonal antibody for 24 hours, at the same ratio as in the CD measurements resulted in the detection by MS-LC of 5–8% of the initial $A\beta_{1-42}$ "monomer" concentration (FIGS. 7A and B and 8A and B).

Example 8

Effects of Aβ Fibers on Cells

Figure 9A:
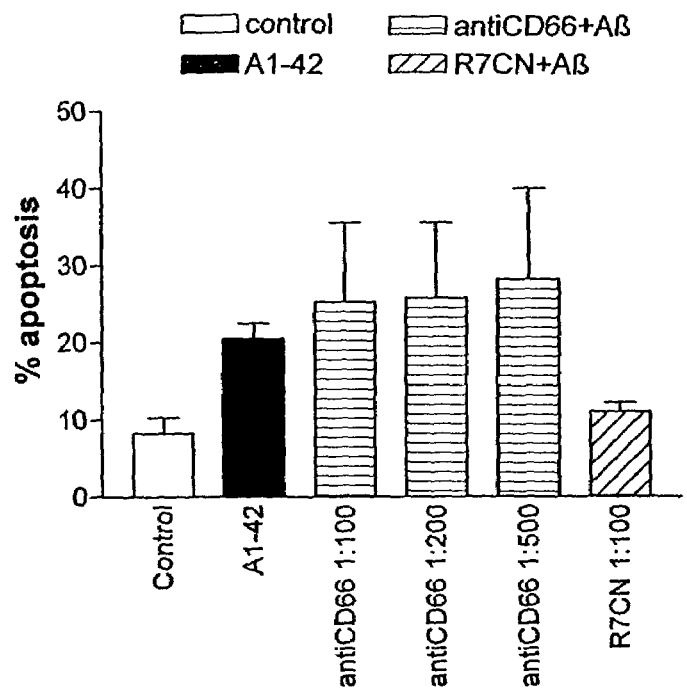
FIG. 9A is a chart of the percent apoptosis of PC12 cells incubated with aggregated $A\beta_{1-42}$ and R7CN or control antibody at different concentrations.

The interaction of $A\beta_{1-42}$ fibers with R7CN was further investigated by cellular methods. In PC12 cells, preaggregated $A\beta_{1-42}$ (final concentration 0.5 mg/l) induced apoptotic cell death after 24 hrs (FIG. 9A). Necrotic cell death could be excluded, by a LDH assay which revealed that lysis of cell membrane occurred only after 48 hrs (data not shown). Preincubation of aggregated $A\beta_{1-42}$ with R7CN at a molar ratio of mAb/Aβ from 1:100 reduced apoptotic cell death in PC12 cells by at least 60% (FIG. 9A).

Example 9

Inhibition of MTT Reduction

Aβ peptides induce an inhibition of MTT reduction. The MTT Cell Proliferation Assay is a colorimetric assay system which measures the reduction of a tetrazolium component (MTT) into an insoluble formazan product by the mitochondria of viable cells. After incubation of the cells with the MTT reagent for approximately 2 to 4 hours, a detergent solution is added to lyse the cells and solubilize the colored crystals. The samples are read using an ELISA plate reader at a wavelength of 570 nm. The amount of color produced is directly proportional to the number of viable cells. his assay is an indicator of the mitochondrial activity of living cells and is a widely used as an index of cytotoxicity. Furthermore, this assay seems to be very sensitive to the neurotoxic effects of Aβ as it has been shown in cell culture experiments after exposure to Aβ fragments already at very low concentrations (Leutz et al., J Mol Neurosci 2002 June; 18(3):189–201; Shearman et al., Proc Natl Acad Sci USA Feb. 15, 1994; 91(4):1470–4).

Figure 9B:
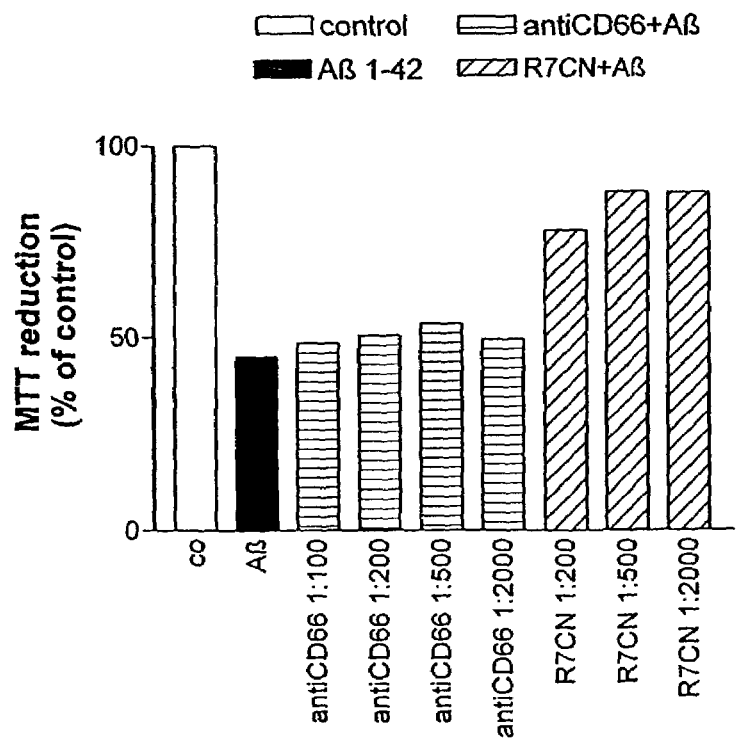
FIG. 9B is a chart of the rate of MTT reduction in PC12 cells incubated with aggregated $A\beta_{1-42}$ and R7CN or control antibody at different concentrations.

At a final concentration of 0.1 µmol/l aggregated $A\beta_{1-42}$ decreased the ability of PC12 cells to reduce MTT by about 60% (FIG. 9B). Incubation of aggregated $A\beta_{1-42}$ with R7CN prevented the $A\beta_{1-42}$-induced collapse in the metabolic activity of PC12 cells (FIG. 9B). The most protective effects have been shown with a mixture of $A\beta_{1-42}$/R7CN that has been generated by incubation of aggregated $A\beta_{1-42}$ with R7CN at a mAb/Aβ ratio from 1:500 up to 1:2000 (FIG. 10B). Incubation with an irrelevant monoclonal antibody had no protective effect, either against $A\beta_{1-42}$ induced apoptosis or on the reduction of MTT. The treatment of aggregated $A\beta_{1-42}$ with anti-Aβ-mAb R7CN markedly reduced Aβ neurotoxicity in vitro. These processes might also contribute to the reduction of Aβ burden in transgenic mice after vaccination.

Example 10

Restoration of Memory by Monoclonal Antibody Treatment

The first time a new object is introduced, normal mice demonstrate an interest in the new object. Any time after the first introduction of the object, the normal mice remember the object and show no interest in it. Mice which are models for human Alzheimer disease, APP London mice, respond in the same manner as normal mice at the first introduction of the object, they show interest in the object. In contrast to normal mice, APP London mice never remember the object and show interest in it every time the object is introduced. There is no memory function in these APP London mice.

The monclonal antibody R7CN was injected i.p. into the APP London mice. When the object was reintroduced to the APP London mice, they responded like the normal mice, and remembered it by showing no interest in the object. The APP London mice showed interest again when a different object was introduced, showing that they still had the ability to respond.

What is claimed is:

1. A composition comprising a monoclonal antibody that binds to B-amyloid protein and induces a conformational change in the protein, wherein the monoclonal antibody is produced by AN-6D4-C1, Accession No. DSM ACC2581, deposited with the DSMZ on Jan. 8, 2003.

2. The composition of claim 1, wherein the conformational change in the protein is from a beta sheet form to an alpha helix form.

3. The composition of claim 1, wherein the monoclonal antibody is R7CN.

4. A monoclonal antibody produced by AN-6D4-C1, Accession No. DSM ACC2581, deposited with the DSMZ on Jan. 8, 2003.

5. The monoclonal antibody of claim 4, wherein the monoclanal antibody is R7CN.

* * * * *